United States Patent
Comings et al.

(10) Patent No.: US 6,743,589 B2
(45) Date of Patent: Jun. 1, 2004

(54) ASSOCIATION OF THE MUSCARINIC CHOLINERGIC 2 RECEPTOR (CHRM2) GENE WITH MAJOR DEPRESSION IN WOMEN

(76) Inventors: David E. Comings, Duarte, CA (US); James P. MacMurray, Loma Linda, CA (US)

( * ) Notice: Subject to any disclaimer, the term of this patent is extended or adjusted under 35 U.S.C. 154(b) by 4 days.

(21) Appl. No.: 10/166,199

(22) Filed: Jun. 11, 2002

(65) Prior Publication Data

US 2003/0087267 A1 May 8, 2003

Related U.S. Application Data

(60) Provisional application No. 60/298,108, filed on Jun. 15, 2001.

(51) Int. Cl.$^7$ ............................ C12Q 1/68; C12P 19/34; C07H 21/02; C07H 21/04
(52) U.S. Cl. ........................ 435/6; 735/91.2; 536/23.1; 536/24.3
(58) Field of Search .................. 435/6, 91.2; 536/23.1, 536/24.3, 23.2

(56) References Cited

U.S. PATENT DOCUMENTS

2002/0187474 A1 * 12/2002 Comings et al. ................ 435/6
2003/0096231 A1 * 5/2003 Landers .......................... 435/6

OTHER PUBLICATIONS

Tasman: Psychiatry, 1$^{st}$ edition, Chapter 54– Depressive Disorders, 1997 W.B. Saunders Company.*
Bonner et al "Identification of a family of muscarinic acetylcholine receptor genes" Science 237 (4814), 527–532 (1987).*
Comings et l "Assocaition of the muscarinic cholinergic 2 receptor (CHRM2) gene with major depression in women" American Journal of Medical Genetics, vol. 114, Issue 5, 2002, abstract.*

T.I. Bonner, et al., "Identification of a Family of Muscarinic Acetylcholine Receptor Genes," Report, Science, vol. 237, Jul. 31, 1987, pp. 527–532.

D.E. Comings, "Polygenic inheritance and micro–minisatellites," Perspective, Molecular Psychiatry 1998 (3), pp. 21–31, 1998 Stock Press.

David E. Comings et al., "Comparison of the role of dopamine, serotonin, and noradrenaline genes in ADHD, ODDD and conduct disorder: multivariate regression analysis of 20 genes," Clinical Genetics 2000: 57, pp. 178–196, Munksgaard 2000.

David E Comings et. al., "Multivariate analysis of associations of 42 genes in ADHD, ODD and conduct disorder," Clinical Genetics 2000: 58, pp. 31–40, Munksgaard 2000.

D. E. Comings et al., "A multivariate analysis of 59 candidate genes in personality traits: the temperament and character inventory," Clinical Genetics 2000: 58; pp. 1–11, Munksgaard 2000.

Zila Welner, M.D. et al., "Reliability, Validity, and Parent-–Child Agreement Studies of the Diagnostic Interview for Children and Adolescents (DICA)," J. Amer. Academic. Child Adolescent. Psychiatry (1987) 26, 5, Reliability and Validity Studies of the DICA, pp. 649–653.

William G. Iacono, et al., "Behavioral disinhibition and the development of substance–use disorders: Findings from the Minnesota Twin Family Study," Development and Psychopathology, 11 (1999), pp. 869–900, 1999 Cambridge University Press, United States.

* cited by examiner

Primary Examiner—Jeffrey Fredman
Assistant Examiner—Teresa Strzelecka

(57) ABSTRACT

The present invention relates to the observation that women having an A→T 1890 polymorphism in the 3' UTR of the cholinergic muscarinic receptor 2 (CHRM2) gene have an increased risk for developing major depression. The present invention provides diagnostic, screening and therapeutic methods based on that observation.

13 Claims, No Drawings

SEQUENCE LISTING

```
<160> NUMBER OF SEQ ID NOS: 3

<210> SEQ ID NO 1
<211> LENGTH: 2210
<212> TYPE: DNA
<213> ORGANISM: Human

<400> SEQUENCE: 1
acatgggaat taggcaggta gacacagtaa tcatgcaggg gaagggagat ttgggagaaa      60
ataatgtggt ttaaaaggag aaacaacatt atgtatttta aaccaatgtt tatattatgt     120
ttgttaattt tattctattt ccttgcaggt ttaaatgttt atttgctact tggctactga     180
ttagagaacg caaaatgaat aactcaacaa actcctctaa caatagcctg gctcttacaa     240
gtccttataa gacatttgaa gtggtgttta ttgtcctggt ggctggatcc ctcagtttgg     300
tgaccattat cgggaacatc ctagtcatgg tttccattaa agtcaaccgc cacctccaga     360
ccgtcaacaa ttacttttta ttcagcttgg cctgtgctga ccttatcata ggtgtttcct     420
ccatgaactt gtacaccctc tacactgtga ttggttactg gcctttggga cctgtggtgt     480
```

-continued

```
gtgacctttg gctagccctg gactatgtgg tcagcaatgc ctcagttatg aatctgctca      540
tcatcagctt tgacaggtac ttctgtgtca caaaacctct gacctaccca gtcaagcgga      600
ccacaaaaat ggcaggtatg atgattgcag ctgcctgggt cctctctttc atcctctggg      660
ctccagccat tctcttctgg cagttcattg taggggtgag aactgtggag gatggggagt      720
gctacattca gttttttttcc aatgctgctg tcacctttgg tacggctatt gcagccttct      780
atttgccagt gatcatcatg actgtgctat attggcacat atcccgagcc agcaagagca      840
ggataaagaa ggacaagaag gagcctgttg ccaaccaaga cccgtttct ccaagtctgg        900 tacaaggaag gatagtgaag ccaaacaata caacatgcc cagcagtgac gatggcctgg        960
agcacaacaa aatccagaat ggcaaagccc ccagggatcc tgtgactgaa aactgtgttc     1020
agggagagga gaaggagagc tccaatgact ccacctcagt cagtgctgtt gcctctaata     1080
tgagagatga tgaaataacc caggatgaaa acacagtttc cacttccctg ggccattcca     1140
aagatgagaa ctctaagcaa acatgcatca gaattggcac caagacccca aaaagtgact     1200
catgtacccc aactaatacc accgtggagg tagtggggtc ttcaggtcag aatggagatg     1260
aaaagcagaa tattgtagcc cgcaagattg tgaagatgac taagcagcct gcaaaaaaga     1320
agcctcctcc ttcccgggaa aagaaagtca ccaggacaat cttggctatt ctgttggctt     1380
tcatcatcac ttgggcccca tacaatgtca tggtgctcat taacaccttt tgtgcacctt     1440
gcatccccca cactgtgtgg acaattggtt actggctttg ttacatcaac agcactatca     1500
accctgcctg ctatgcactt tgcaatgcca ccttcaagaa gacctttaaa caccttctca     1560
tgtgtcatta taagaacata ggcgctacaa ggtaaaatat ctttgaaaaa gatagaaggt     1620
gggcaagggg agcttgagaa gaataaaagg gataaacgag ctcctagttt taaaatctct     1680
gccattgcac tttatagtct gattacaaaa cgtgcaattc aggagcccag cagtgacaca     1740
cttatcacgc ctaggctcca gtttgcaaaa attgcacctt ataaactgtc agtattagga     1800
gcaatgagac aatgaaagaa acatgttggg atcgtggatt taagaaacta tacactgttt     1860
ctcataatct cttgaagaag ggcttctgat tctacaattt tatcagtctc tgcacaagag     1920
gaataacctt gttcctttt tgttacttttt gttgttgttg ttctcatgtg tccttaagag     1980
aaggaatgcc acagttacaa ggtaaacatg gagacttaaa cataaagaaa taggcactat     2040
acaatgggga cataaaaaaa gaaaatgaaa gaaggatgca gaaatttgtc tccggagtgt     2100
taagcatatt ttattctttt gttacggtcc tatttagagg attggaatgt aataaatgct     2160 tatttttttgc ctttctttt cccaccatga agagaaagca aacaaacaga                 2210
```

<210> SEQ ID NO 2
<211> LENGTH: 21
<212> TYPE: DNA
<213> ORGANISM: human

<400> SEQUENCE: 2
acaaaacgtg caattcagga g                                                 21

<210> SEQ ID NO 3
<211> LENGTH: 21
<212> TYPE: DNA
<213> ORGANISM: Human

<400> SEQUENCE: 3
cagagactga taaaattgta g                                                 21

ASSOCIATION OF THE MUSCARINIC CHOLINERGIC 2 RECEPTOR (CHRM2) GENE WITH MAJOR DEPRESSION IN WOMEN

CROSS-REFERENCES TO RELATED APPLICATIONS

The present application is related to U.S. provisional application Ser. No. 60/298,108 filed Jun. 15, 2001, incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to screening patients to determine their risk for having major depression.

2. Description of the Related Art

A bibliography follows at the end of the Detailed Description of the Invention. The listed references are all incorporated herein by reference.

The lifetime frequency of major depression (MD) is twice as high in women as in men (1). Twin studies have shown a significant genetic contribution to MD in women with heritabilities ranging from 0.33 to 0.45 and higher (2–5), and an important role of stress (6). Some twin studies have suggested a comparable heritability for men and women (4), while others have suggested a greater heritability for women (5). In 1972 and again in 1994, Janowsky (8, 9) reviewed the evidence for a role of cholinergic hypersensitivity in depression. Both REM and non-REM sleep is regulated by cholinergic, serotonergic and noradrenergic neurons in the brain stem (10). The early onset of REM sleep, increased REM density and exaggerated REM response to cholinergic stimulation in depression, is consistent with CNS cholinergic overactivity or muscarinic supersensitivity in depression (10). While the HPA axis has been emphasized in the response to stress, recent studies of Kaufer, et al. (11) have identified an important alternative cholinergic pathway. They showed that acute stress resulted in an immediate increase in synaptosomal acetylcholine with neuronal excitability, with a delayed phase response of increased expression of acetylcholineaserase, decreased choline acetyl transferase and vesicular acetylcholine transporter (CHAT) activity and a resulting decrease in neuronal excitability (11, 12). Others have also emphasized the important role of stress in activating muscarinic systems (13).

BRIEF SUMMARY OF THE INVENTION

In one aspect, the present invention relates to a method for screening a patient to determine whether such patient is at increased risk for developing major depression, said method comprising analyzing a sample of said patient's genetic material to determine the patient's genotype with respect to the cholinergic muscarinic receptor 2 (CHRM2) gene, wherein the presence of a T at nucleotide number 1890 in the 3' UTR of said gene correlates with an increased risk for developing major depression.

In another aspect, the present invention relates to a method for diagnosing major depression in a patient, said method comprising analyzing a sample of a patient's genetic material to determine to determine the patient's genotype with respect to the cholinergic muscarinic receptor 2 (CHRM2) gene, wherein the presence of a T at nucleotide number 1890 in the 3' UTR of said gene is indicative of the presence of major depression.

In another aspect, the present invention relates to a method for screening a subject to determine whether such subject is a candidate for a therapy using a drug which prevents or treats a disorder associated with the presence of a T at nucleotide number 1890 in the 3' UTR of the cholinergic muscarinic receptor 2 (CHRM2) gene, said method comprising determining the subject's genotype with respect to such gene, wherein a subject having a T at said nucleotide number is a candidate for such therapy.

In another aspect, the present invention relates to a method for treating a patient having or at increased risk for developing major depression associated with the presence of a T at nucleotide number 1890 in the 3' UTR of the cholinergic muscarinic receptor 2 (CHRM2) gene, said method comprising administering to said patient an effective amount of a material which diminishes the effect of such gene.

In another aspect, the present invention relates to a method for identifying materials that can be used in the treatment of a patient having or at increased risk for developing a disorder associated with the presence of a T at nucleotide number 1890 in the 3' UTR of the cholinergic muscarinic receptor 2 (CHRM2) gene, said method comprising determining whether the material is capable of diminishing the effect of such gene.

In another aspect, the present invention relates to a pharmaceutical composition which comprises a) an effective amount of a material which is capable of diminishing the effect of the cholinergic muscarinic receptor 2 (CHRM2) gene having a T at nucleotide number 1890 in the 3' UTR; and b) a pharmaceutically acceptable carrier.

In another aspect, the present invention relates to a kit suitable for screening a subject to determine whether such subject is at increased risk for having or developing a disorder associated with the presence of a T at nucleotide number 1890 in the 3' UTR of the cholinergic muscarinic receptor 2 (CHRM2) gene, said kit comprising a) material for determining the subject's genotype with respect to said gene;

b) suitable packaging material; and optionally c) instructional material for use of said kit.

DETAILED DESCRIPTION OF THE INVENTION

The present invention is based on the observation that subjects, particularly females, having a T at nucleotide number 1890 in the 3' UTR of the cholinergic muscarinic receptor 2 (CHRM2) gene have an increased risk of having major depression.

The present invention entails the determination of the subject's genotype with respect to the CHRM2 gene. That gene is located on chromosome 7q31-q35. See reference (23) and the references cited therein, the contents of which are incorporated herein by reference. The relevant portion of the sequence is as follows (the T nucleotide at position 1890 is indicated in bold type): acatgggaat taggcaggta gacacagtaa tcatgcaggg gaagggagat 50
ttgggagaaa ataatgtggt ttaaaaggag aaacaacatt atgtatttta 100
aaccaatgtt tatattatgt ttgttaattt tattctattt ccttgcaggt 150
ttaaatgttt atttgctact tggctactga ttagagaacg caaaatgaat 200
aactcaacaa actcctctaa caatagcctg gctcttacaa gtccttataa 250
gacatttgaa gtggtgttta ttgtcctggt ggctggatcc ctcagtttgg 300
tgaccattat cgggaacatc ctagtcatgg tttccattaa agtcaaccgc 350
cacctccaga ccgtcaacaa ttacttttta ttcagcttgg cctgtgctga 400
ccttatcata ggtgttttct ccatgaactt gtacaccctc tacactgtga 450
ttggttactg gcctttggga cctgtggtgt gtgacctttg gctagccctg 500
gactatgtgg tcagcaatgc ctcagttatg aatctgctca tcatcagctt 550
tgacaggtac ttctgtgtca caaacctct gacctaccca gtcaagcgga 600
ccacaaaaat ggcaggtatg atgattgcag ctgcctgggt cctctctttc 650
atcctctggg ctccagccat tctcttctgg cagttcattg taggggtgag 700
aactgtggag gatggggagt gctacattca gtttttttcc aatgctgctg 750
tcacctttgg tacggctatt gcagcctct atttgccagt gatcatcatg 800
actgtgctat attggcacat atcccgagcc agcaagagca ggataaagaa 850
ggacaagaag gagcctgttg ccaaccaaga ccccgtttct ccaagtctgg 900
tacaaggaag gatagtgaag ccaaacaata acaacatgcc cagcagtgac 950
gatggcctgg agcacaacaa aatcca- gaat ggcaaagccc ccagggatcc 1000
tgtgactgaa aactgtgttc agg- gagagga gaaggagagc tccaatgact 1050
ccacctcagt cagtgctgtt gcctctaata tgagagatga tgaaataacc 1100
caggatgaaa acacagtttc cacttccctg ggccattcca aagatgagaa 1150
ctctaagcaa acatgcatca gaattggcac caagacccca aaaagtgact 1200 catgtaccc aac- taatacc accgtggagg tagtggggtc ttcaggtcag 1250
aatggagatg aaaagcagaa tattgtagcc cgcaagattg tgaagatgac 1300 taag- cagcct gcaaaaaaga agcctcctcc ttcccgggaa aagaaagtca 1350
ccaggacaat cttggctatt ctgttggctt tcatcatcac ttgggcccca 1400
tacaatgtca tggtgctcat taacacctt tgtgcacctt gcatcccaa 1450 cactgtgtgg acaattggtt actggctttg ttacatcaac agcactatca 1500
accctgcctg ctatgcactt tgcaatgcca ccttcaagaa gacctttaaa 1550
caccttctca tgtgtcatta taagaacata ggcgctacaa ggtaaaatat 1600
ctttgaaaaa gatagaaggt gggcaagggg agcttgagaa gaataaaagg 1650
gataaacgag ctcctagttt taaaatctct gccattgcac tttatagtct 1700
gattacaaaa cgtgcaattc aggagcccag cagtgacaca cttat- cacgc 1750 ctaggctcca gtttgcaaaa attgcacctt ataaactgtc agtattagga 1800
gcaatgagac aatgaaagaa acatgttggg atcgtg- gatt taagaaacta 1850 tacactgttt ctcataatct cttgaagaag ggcttct- gat tctacaattt 1900 tatcagtctc tgcacaagag gaataaccctt gttcctttt 1950 gttgttgttg ttctcatgtg tccttaagag aaggaatgcc acagttacaa 2000
ggtaaacatg gagacttaaa cataaagaaa taggcac- tat acaatgggga 2050 cataaaaaaa gaaaatgaaa gaaggatgca gaaatttgtc tccggagtgt 2100
taagcatatt ttattctttt gttacggtcc tatttagagg atttggaatgt 2150 aataaatgct tattttttgc ctttctttt cccaccatga agagaaagca 2200 aacaaacaga 2210 [SEQ ID NO:1].

Such can be determined, for example, by analysis of the subject's DNA. Suitable analysis techniques are well known to those in the art, and include amplification genotyping (amplification of the desired region by suitable methods, such as PCR, followed by electrophoresis), in situ hybridization techniques, direct DNA sequencing, etc.

A further aspect of the present invention is the treatment of a disorder associated with the presence of the allele described herein, to prevent the development or progression of such disorder. The patient is administered an effective amount of a material which diminishes or eliminates the adverse effects of the allele. The material may act in a number of ways which would be apparent to one of ordinary skill. For example, it may act to decrease the production of the protein, such as by affecting the DNA or RNA responsible for protein production, or by affecting regulatory elements. One way to accomplish diminished protein production is by introduction via gene therapy or gene repair techniques of a gene or gene segment which converts the allele associated with the disorder into a benign allele. See, for example, the techniques described in U.S. Pat. No. 5,776,744, the contents of which are incorporated herein by reference. The material may also act by directly or indirectly affecting the produced protein to diminish the protein's activity or effect.

It will be apparent that the information regarding a subject's genotype with respect to the CHRM2 gene may also be used to determine whether the subject is a candidate for a therapy using a drug which prevents or treats a disorder associated with the CHRM2 gene in question.

For therapeutic treatment, the materials of the present invention may be formulated into a pharmaceutical composition, which may include, in addition to an effective amount of the active ingredient, pharmaceutically acceptable carriers, diluents, buffers, preservatives, surface active agents, and the like. Compositions may also include one or more other active ingredients if necessary or desirable.

The pharmaceutical compositions of the present invention may be administered in a number of ways as will be apparent to one of ordinary skill in the art. Administration may be done topically, orally, by inhalation, or parenterally, for example.

Topical formulations may include ointments, lotions, creams, gels, drops, suppositories, sprays, liquids and powders. Oral formulations include powders, granules, suspensions or solution in water or non-aqueous media, capsules or tablets, for example. Thickeners, flavorings, diluents, emulsifiers, dispersing aids or binders may be used as needed.

Parenteral formulations may include sterile aqueous solutions which may also contain buffers, diluents and other suitable additives.

The dose regimen of the compounds or compositions of the present invention will depend on a number of factors which may readily be determined, such as severity and responsiveness of the condition to be treated.

The present invention also provides a screening method for identifying materials that may be used in the treatment of a patient having or at increased risk for developing a disorder associated with the presence of the CHRM2 gene having a T at nucleotide number 1890 in the 3' UTR. In practice of such a method, a candidate material is screened in an assay which determines whether the material is capable of diminishing the effect of the gene in question. Suitable assays would be readily apparent to one of ordinary skill, including animal models and in vitro assays. The assays may be designed to test, for example, the effect of the material on the production of the particular protein, or its effect on the activity of the protein.

The present invention also provides a kit suitable for screening a subject for any of the purposes described above. The kit comprises material for determining the subject's genotype with respect to the CHRM2 gene. Preferably, such material comprises at least two primers capable of hybridizing to a region flanking nucleotide number 1890 in the 3' UTR segment of the CHRM2 gene. The primers preferably are suitable for use in an amplification reaction, such as PCR. The kit additionally contains suitable packaging material, and optionally contains instructional material for use of the kit, result interpretation, etc. The kit may also contain additional reactants suitable for use with the primers, such as appropriate concentrations of deoxynucleotide triphosphates, suitable buffers, polymerization enzymes, etc.

The following non-limiting examples are illustrative of the processes and products of the present invention.

EXAMPLE 1

Subjects. The sample consisted of 760 non-Hispanic Caucasian adults from the Minnesota Twin and Family Study (MTFS) (14). The MTFS is a large, multi-discipline, multi-year study to examine the interaction between genetic and environmental risk factors in the development of adolescent and adult alcoholism and drug abuse. The advantage of the study is that it uses a population based twin ascertainment in which all same sex twins born in the state of Minnesota are identified by public birth records. The recruitment targets 11 and 17 year old twins. Of the eligible families only 17% declined invitations to participate. The present study was restricted to the parents of the twins. They were administered the parent version of the DICA-R (Diagnostic Interview for Children and Adolescents (15) and the Structured Clinical Interview for DSM-III-R (SCID-R) (16). Interviews were administered by individuals who have a bachelor's or master's degree in psychology or a related field. Interviewers also complete an intensive course of training that includes didactic instruction, practice interviews, mentoring by an experienced clinical interviewer, and a written examination covering the DSM disorders assessed. All interviews are tape-recorded. Complete interviews are reviewed in a consensus conference by at least two advanced clinical psychology graduate students. Individual symptoms are reviewed, including listening to the audio tapes as needed, to determine whether the behaviors reported by the interviewees were frequent and severe enough to count as a symptom under DSM. In a study of the reliability of the diagnostic and consensus procedures that involved review of clinical material by two independent teams for clinicians, the kappa coefficient for the depression diagnosis was estimated at 0.82 (14).

We genotyped 430 women and 330 men. Of these, 126 of the women and 52 of the men had a DSM-IIIR diagnosis of definite lifetime MD.

Genotyping. Using the SSCP technique (17) we identified a common single nucleotide polymorphism, A→T 1890 in the 3' UTR of the CHRM2 gene based on accession # M16404. The upstream primer was 5'-ACAAAACGTG CAATTCAGGA G-3' [SEQ ID NO:2]. The downstream primer was 5'-CAGAGACTGA TAAAATTGTA G-3' [SEQ ID NO:3]. The PCR reaction consisted of QIAGEN 10x PCR buffer 2.0 $\mu$l, 0.4 $\mu$l of 10 mM dNTP, 0.4 $\mu$l of 10 $\mu$M each primer, 0.5 units of Taq polymerase, ddH$_2$O16.1 $\mu$l and 50 ng DNA in total volume of 20 $\mu$l. Amplification consisted of 30 cycles with denaturation at 95° C. for 30 seconds, annealing temperature 54° C. for 1 minute, and extension at 72° C. for 1 minute. This produced a 208 bp product, which was digested with Dpn II restriction endonuclease using 1 ul 10x New England Biological (NEB) enzyme buffer, 0.3 $\mu$l of Dpn II, 3.7 $\mu$l of double distilled H$_2$0, and 5 $\mu$l PCR product incubated at 37° C. for 3 hours. The product were visualized by electrophoresis in 10% acrylamide gel. The A allele gave 81 and 127 bp products. The T allele gave 58+23 and 127 bp products.

Statistics. The frequency of the 11, 12 and 22 genotypes in male and female subjects with and without a diagnosis of MD was compared by Chi square analysis. A Bonferroni corrected a of 0.025 was used. To determine the percent of the variance of MD, accounted for by the CHMR2 gene, we scored those with the 11 genotype as 1, and those with the remaining two genotypes as 0. Those without MD were scored as 0, and those with MD as 1. The presence or absence of MD was the dependent variable and the gene score was the independent variable in a linear regression analysis. The SPSS statistical package was used (SPSS, Inc, Chicago, Ill.).

Results

The results are shown in Table 1. For the women without MD, 25.7% carried the 11 genotype compared to 43.7% for with MD. There was a proportionate decrease in the frequency of the other two genotypes ($\chi^2$=13.53, d.f.=1., p=0.001). By contrast for men, while the frequency of the 11 genotype in those without MD was similar to that for the women (27.7%), there was no increase in frequency for the 11 genotype for those with MD (26.9%, $\chi^2$=1.48, d.f.=1., p=0.47). The CHRM2 alleles were in Hardy-Weinberg equilibrium for those without MD. Regression analysis showed that in women $r^2$=0.030, F=13.37, p=0.0003. By contrast, in men $r^2$=0.00001, F=0.002, p=0.96.

Discussion

These results suggest that CHRM2 may be a gene associated with MD in women but not in men. This association with MD is consistent with the postulated role of enhanced or hypersensitive cholinergic systems in depression (8, 9). The association of cholinergic systems with REM sleep (10, 18), and the disturbance of REM sleep in individuals with depression are consistent with the presence of genetic defects in the cholinergic system in MD.

In women, the CHRM2 gene accounted for 3 percent of the variance of MD while in men it accounted for virtually none of the variance. The increased frequency of MD in females, and some twin studies (5) suggesting a greater heritability of MD in women, raise the possibility that the CHRM2 is a gender specific gene for MD. While the mechanism by which a non-X-linked gene would have this effect is not known, there are several possibilities. These include hormone responsive promoters or enhancers, affecting either CHRM2 other genes that interact with CHRM2. A second possibility is that if women are more sensitive to stress expressed through the cholinergic stress pathway (11, 12, 13), they would also be more likely to show an association between the CHRM2 gene and depression.

Since the A/T polymorphism was in the 3' region of the CHRM2 gene we assume it was in linkage disequilibrium with alleles affecting gene function, possibly microsatellites (19). The fact that even though the CHRM2 gene accounted for only 3 percent of the variance of MD in women, even though the association was significant, is an expected characteristic of a complex polygenic disorder where multiple genes are involved and each accounts for only a small percent of the variance. In our experience, 3 percent is a higher than the average $r^2$ for most gene-phenotype associations for behavioral disorders (20, 21, 22).

Table 1. Association of the CHRM2 Gene with Major depression in women and men in the Minnesota Twin and Family Study

TABLE 1

Association of the CHRM2 Gene with Major depression in women and men in the Minnesota Twin and Family Study

| | N | CHRM2 genotypes | | | $X^2$ | p |
| --- | --- | --- | --- | --- | --- | --- |
| | | 11 | 12 | 22 | | |
| Women | | | | | | |
| No MD | 304 | 78 (25.7) | 159 (52.3) | 67 (22.0) | | |
| Definite MD | 126 | 55 (43.7) | 49 (38.9) | 22 (17.5) | 13.53 | .001 |
| Total | 430 | | | | | |
| Men | | | | | | |
| No MD | 278 | 77 (27.7) | 122 (43.9) | 79 (28.4) | | |
| Definite MD | 52 | 14 (26.9) | 27 (51.9) | 11 (21.2) | 1.48 | .47 |
| Total | 330 | | | | | |

REFERENCES

1. Weisman M M, et al. (1991) Affective Disorders. In Robins L N, Regier D A (eds) *Psychiatric Diosrders in America*. New York: The Free Press.

2. Kendler, K S, Neale, M C, Kessler, R C, Heath, A C, and Eaves, L J (1993). The longitudinal twin study of personality and major depression in women. *Arch. Gen. Psychiatry* 50:853–862.
3. Kendler, K S, Neale, M C, Kessler, R C, Heath, A C, and Eaves, L J (1993). The lifetime history of major depression in women. Reliability of diagnosis and heritability. *Arch. Gen. Psychiatry* 50:863–870.
4. Kendler, K S and Prescott, C A (1999). A population-based twin study of lifetime major depression in men and women. *Arch. Gen. Psychiatry* 56:39–44.
5. Bierut, L J, Heath, A C, Bucholz, K K, Dinwiddie, S H, Madden, P A, Statham, D J, Dunne, M P, and Martin, N G (1999). Major depressive disorder in a community-based twin sample: are there different genetic and environmental contributions for men and women? *Arch. Gen. Psychiatry* 56:557–63.
6. Kendler, K S, Kessler, R C, Walters, E E, MacLean, C, Neale, M C, Heath, A C, and Eaves, L J (1995). Stressful life events, genetic liability, and onset of an episode of major depression in women. *Am J Psychiatry* 152:833–42.
7. Kendler, K S, Thornton, L M, and Gardner, C O (2000). Stressful life events and previous episodes in the etiology of major depression in women: an evaluation of the "kindling" hypothesis. *Am J Psychiatry* 157 (8):1243–51.
8. Janowsky, D S, Overstreet, D H, and Nurnberger, J I Jr (1994). Is cholinergic sensitivity a genetic marker for the affective disorders? *Am J Med Genet* 54 (4):335–44.
9. Janowsky, D S, El-Yousef, M K, Davis, J M, and Sekerke, H J (1972). A cholinergic-adrenergic hypothesis of mania and depression. *Lancet* 1:632.
10. Riemann, D, Hohagen, F, Bahro, M, Lis, S, Stadmuller, G, Gann, H, and Berger, M (1994). Cholinergic neurotransmission, REM sleep and depression. *J Psychosom Res* 38 Suppl 1:15–25.
11. Kaufer, D, Friedman, A, Seldman, S, and Soreq, H (1998). Acute stress facilitates long-lasting changes in cholinergic gene expression. *Nature* 393:373–381.
12. Sapolsky, R M (1998). The stress of Gulf War syndrome. *Nature* 393:308–309.
13. Dilsaver, S C (1988). Effects of stress on muscarinic mechanisms. *Neurosci Biobehav Rev* 12:23–28.
14. Iacano, W G, Carlson, S R, Taylor, J, Elkins, I J, and McGue, M. (1999) Behavioral disinhibition and the development of substance-use disorders: Findings from the Minnesota Twin Family Study. *Development and Psychopathology* 11, 869–900.
15. Weiner, Z, Reich, W, Herjanic, B, Jung, K, and Amado, H (1987). Reliability, validity, and parent-child agreement studies of the Diagostic Interview for Children and Adolescents (DICA). *J. Amer. Acad. Child Adolescent Psychiat.* 26:649–653.
16. Spitzer R L, Williams J B W, Gibbon M. (1987). Structured Clinical Interview for DSM-III-R. New York: Elsevier Science Publishers.
17. Orita, M, Iwahana, H, Kanazawa, H, Hayashi, K, and Sekiya, Y (1989). Detection of polymorphisms of human DNA by gel electrophoresis as single-strand conformation polymorphisms. *Proc. Natl. Acad. Sci. U.S.A.* 86:2766–2770.
18. Gillin, J C, Sitaram, N, and Duncan, W C (1979). Muscarinic supersensitivity: a possible model for the sleep disturbance of primary depression? *Psychiatry Res* 1:17–22.
19. Comings, D E (1998). Polygenic inheritance and micro/minisatellites. *Molecular Psychiatry* 3:21–31.
20. Comings, D E, et al. (2000). Comparison of the role of dopamine, serotonin, and noradrenergic genes in ADHD, ODD and conduct disorder. Multivariate regression analysis of 20 genes. *Clinical Genetics* 57:178–196.
21. Comings, D E, et al. (2000). Multivariate Analysis of Associations of 42 Genes in ADHD, ODD and Conduct Disorder. *Clinical Genetics* 58:31–40.
22. Comings, D E, et al. (2000). A Multivariate Analysis of 59 Candidate Genes in Personality Traits: The Temperament Character Inventory. *Clinical Genetics* 58:375–385.
23. Bonner, T I, et al. (1987) Identification of a family of muscarinic acetylcholine receptor genes. *Science* 237 (4814), 527–532 [published erratum appears in *Science* Sep. 25, 1987; 237 (4822) :237] (1987)

What is claimed is:

1. A method for screening a female patient to determine whether such patient is at increased risk for developing major depression, said method comprising analyzing a sample of said patient's genetic material to determine the patient's genotype with respect to the cholinergic muscannic receptor 2 (CHRM2) gene, wherein the presence of a T at nucleotide number 1890 in the 3' untranslated region (3' UTR) of said gene [SEQ ID. NO:1] correlates With an increased risk for developing depression.

2. The method of claim 1, wherein the analysis utilizes an amplification reaction.

3. The method of claim 2, wherein the amplification reaction utilizes PCR.

4. The method of claim 3, wherein the PCR reaction utilizes a primer selected from the group consisting of SEQ ID NO:2 and SEQ ID NO:3.

5. A method for diagnosing major depression in a female patient, said method comprising analyzing a sample of a female patient's genetic material to determine the patient's genotype with respect to the cholinergic muscarinic receptor 2 (CHRM2) gene, wherein the presence of a T at nucleotide number 1890 in the 3' untranslated region (3' UTR) of said gene [SEQ ID NO: 1] is indicative of the presence of major depression.

6. The method of claim 5, wherein the analysis utilizes an amplification reaction.

7. The method of claim 6, wherein the amplification reaction utilizes PCR.

8. The method of claim 7, wherein the PCR reaction utilizes a primer selected from the group consisting of SEQ ID NO:2 and SEQ ID NO:3.

9. A method for testing a sample of female human genetic material, said method comprising the step of determining whether a T is present at nucleotide number 1890 in the 3' untranslated region (3' UTR) of the cholinergic musearinic receptor 2 (CHRM2) gene [SEQ ID NO: 1].

10. The method of claim 9, wherein the determination utilizes an amplification reaction.

11. The method of claim 10, wherein the amplification reaction utilizes PCR.

12. The method of claim 11, wherein the PCR reaction utilizes a primer selected from the group consisting of SEQ ID NO:2 and SEQ ID NO:3.

13. A kit suitable for screening a female subject to determine whether such subject is at increased risk for having or developing major depressive disorder associated with the presence of a T at nucleotide number 1890 in the 3' untranslated region (3' UTR) of the cholinergic muscarinic receptor 2 (CHRM2) gene [SEQ ID NO:1], said kit comprising a) material for determining the subject's genotype with respect to said gene;

b) suitable packaging material; and optionally c) instructional material for use of said kit wherein item a) comprises at least one PCR primer selected from the group consisting of SEQ ID NO: 2, SEQ ID NO: 3, and combinations thereof.

* * * * *

UNITED STATES PATENT AND TRADEMARK OFFICE
CERTIFICATE OF CORRECTION

PATENT NO. : 6,743,589 B2  
DATED : June 1, 2004  
INVENTOR(S) : David E. Comings et al.

It is certified that error appears in the above-identified patent and that said Letters Patent is hereby corrected as shown below:

Title page,  
Item [73], Assignee, please insert -- City of Hope, Duarte, California; --  
Item [56], References Cited, U.S. PATENT DOCUMENTS, "Comings et l" should be -- Comings et al. --;

Column 8,  
Line 8, "Weiner" should be -- Welner --;

Column 12,  
Line 26, insert a comma after "said kit".

Signed and Sealed this

Fifteenth Day of March, 2005

JON W. DUDAS  
*Director of the United States Patent and Trademark Office*